United States Patent [19]

Yunker et al.

[11] 4,447,537

[45] May 8, 1984

[54] TICK CELL LINES

[75] Inventors: Conrad E. Yunker; John C. Cory, both of Hamilton; Harold R. Meibos, Darby, all of Mont.

[73] Assignee: The United States of Americas as represented by the Department of Health and Human Services, Washington, D.C.

[21] Appl. No.: 227,166

[22] Filed: Jan. 22, 1981

[51] Int. Cl.$^3$ ..................... A61K 39/00; A61K 39/12
[52] U.S. Cl. .................................... 435/235; 424/88; 424/89
[58] Field of Search ............. 435/240, 243, 253, 260, 435/258, 235, 948; 424/88, 89, 93

[56] References Cited

U.S. PATENT DOCUMENTS

| | | | |
|---|---|---|---|
| 2,658,021 | 11/1953 | Earle et al. | 435/240 |
| 3,647,633 | 3/1972 | Dawson | 435/286 |
| 3,709,782 | 1/1973 | Smith et al. | 435/240 |
| 4,017,631 | 4/1977 | Febvre et al. | 435/241 |
| 4,021,302 | 5/1977 | Smith et al. | 435/240 |
| 4,040,905 | 8/1977 | Petricciani | 435/240 |

OTHER PUBLICATIONS

Bhat et al., Experientia 35, 752 (1979).
Kurtti et al., in *Practical Tissue Culture Applications,* Maramorosch et al., (eds.), Academic Press, 1979, pp. 351–371.
Andreasen, Acta Path. Microb. Scand., Sec. B 82, pp. 455–456 (1974).
Ball, et al., J. Parasitology, vol. 59, No. 3, pp. 513–515 (1973).
Bhat & Yunker, J. Parasitology, vol. 63, No. 6, pp. 1092–1098 (1977).
Buckley, "Invertebrate Tissue Culture, Research Applications", Acad. Press, N.Y., (1976), pp. 201–232.
Article by Davey, et al., J. Gen. Virol, 24, pp. 453–463 (1974).
Article by Hadani, et al., J. Parasitology, 64 (3), pp. 501–503 (1978).
Article by Hink in "Invertebrate Tissue Culture, Research Applications", Acad. Press. N.Y. (1976), at pp. 319–369.
Article by Hoffman, Z. Angew. Entomol., 71:26–34 (1972), [with English translation by NIH Library #NIH-77-164C].
Article by McCall in "Tick–Borne Diseases and Their Vectors", U. of Edinburgh (1978), at pp. 343–350.
Article by Pudney, et al., in TCA Manual, vol. 5, Mo. 1 (1979), pp. 1003–1007.
Article by Rehacek and Brezina, Acta. Virol, 8:380 (1964).
Article by Rehacek, et al., Acta. Virol. 12:41–43 (1968).
Article by Tully, et al., Science, vol. 212, pp. 1043–1045 (1981).
Article by Vaughn in "Invertebrate Tissue Culture, Research Applications", Acad. Press, N.Y. (1976), at pp. 295–303.
Article by Yunker in "Current Topics in Microbiology", Springer-Verlag, N.Y. (1971), at pp. 113–126, references at pp. 249–268.
Article Abstract and Covering Sheet by Yunker, et al., TCA 31 st Annual Meeting (1980), No. 78.
Article by Yunker, et al., In Vitro, 17 (2), pp. 139–142 (Feb. 1981).
Article by Yunker, et al., TCA Manual, vol. 5, No. 1 (1979), pp. 1015–1017.

*Primary Examiner*—Thomas G. Wiseman
*Assistant Examiner*—James Martinell
*Attorney, Agent, or Firm*—Holman & Stern

[57] ABSTRACT

Six new cell lines of Acari: Ixodidae are provided, four from embryonic tissue of *Dermacentor variabilis* and two from embryonic tissue of *Dermacentor parumapertus;* and the use of these cell lines for replicating representative microorganisms is shown.

18 Claims, No Drawings

TICK CELL LINES

BACKGROUND OF THE INVENTION

1. Field of the Invention

This invention relates to new continuous cell lines from embryonic tissues of ticks (*Acari Ixodidae*); the use of such cells lines for replicating selected microorganisms; and the use of the replicated microorganisms for diagnosis, prophylaxis and control of diseases in vertebrate animals caused by infections of such microorganisms.

2. Description of the Prior Art

Tissue culture and cloning of pure cell strains is an established art, dating back to the in vitro growth and differentiation or nerve cells from an embryo by Harrison in 1909. Many cells lines of arthropods of the class Insecta have successfully been established, but relatively few of the class Arachnida. In particular, few cell lines of the order Acari (Mites and Ticks) and very few of the family Ixodidae (Ticks) are known. For example, Hink in "Invertebrate Tissue Culture, Research Applications", Acad. Press, N.Y., 1976, Pp. 319–369, stated that only 5 cell lines from 3 species of Acarina were known, as contrasted with 24 cell lines from 15 species of Lepidoptera and 63 cell lines from 21 species of Diptera. There are various reasons for this, including the extremely delicate microbiology of cells, which is evidenced by extreme sensitivity to culture culture medium and conditions. As a result of this sensitivity, culture media and conditions suitable for cells of a closely related family such as Parasitidae (Dung Beetle Mites) may not also be suitable for Ixodidae (Ticks).

Ticks, because of their complex life cycles in which one or more blood meals are required for each feeding stage, are the most important vectors of infectious disease to vertebrate animals and are second only to mosquitoes as vectors of disease to man. Among the diseases transmitted by ticks are hemorrhagic fevers and other viroses, rickettsioses, anaplasmosis, piroplasmosis, spirochaetosis, tularemia and filariasis. In vitro cultures of tick tissues and cells have obvious benefits for the study of the causal agents of tickborne disease. The few continuous lines of tick cells that have been established are difficult to manage because of slow growth and the fastidious nature of the cells. Such cell lines were disclosed by Varma, Pudney, and Leake, "The Establishment of Three Cell Lines from the Tick *Rhipicephalus appendiculatus* (Acari: Ixodidae) and Their Infection with some Arboviruses", J. Med. Entomol., 11:698–706, (1975); and by Bhat and Yunker, "Establishment and Characterization of a Diploid Cell Line from the Tick *Dermacentor parumapertus* Neumann (Acarina: Ixodidae)", J. Parasitol., 63:1092–1098 (1977). The cell line of Bhat and Yunker, 1977, above, has accidentally been extinguished by toxic culture medium and bacterial contamination of frozen stocks.

The general technique for culturing embryonic tick cells used for the cell lines of this invention was disclosed by Yunker and Meibos in "Culture of Embryonic Tick Cells (Acari: Ixodidae)", Tissue Culture Association (TCA) Manual, Vol. 5, No. 1, 1979. Similar disclosure will be found in Bhat and Yunker, 1977, above, and in Pudney, Varma, and Leake, "Establishment of Cell Lines from Ixodid Ticks", TCA Manual, Vol. 5, No. 1, 1979.

The general use of tissue cell lines for the culture or replication of pathogenic microorganisms is well established, although the use of arthropod vector cell lines for culturing zoonotic disease agents is relatively rare. Due to the biochemical nature of microorganisms, especially viruses and rickettsias, specific microorganisms can not be cultured in all cell lines, even in all cell lines from the same order.

Buckley, in "Invertebrate Tissue Culture, Research Applications", Acad. Press. New York and London, (1976), Pp. 201–32 (Chapter 12—Arboviruses and *Toxoplasma gondii* in Diptera Cell lines), discloses replications of various arthropod vector viruses in mosquito cell lines. She explicitly recognizes marked innate differences between individual cell lines (p. 202) and notes, for example, that several tick viral isolates have failed to propagate in Aedes (mosquito) cell lines (p. 205) while Ganjam virus, isolated from both mosquitoes and ticks, multiplied in the *Aedes albopictus* cell line but not in the *Aedes aegypti* cell line (p. 204).

Also similarly, Vaughn in "Invertebrate Tissue Culture, Research Applications", Acad. Press, New York and London (1976) at Pp. 295–303 (Chapter 15—The Production of Viruses for Insect Control in Large Scale Cultures of Insect Cells) discusses the development of insect cell lines and notes that, for example, cell lines from *Heliothis zea* are not capable of complete replication of the nuclear polyhedrosis virus obtained from the *Heliothis zea* itself.

From the above, it should be apparent that the ability of a given cell line to replicate successfully a given microorganism, especially a virus or rickettsia, cannot be predicted from results in cell lines of different species. In fact, because of cellular adaptation, even cell lines from the same species may not be equally useful for microorganism replication.

Viruses are "submicroscopic entities capable of being introduced into specific living cells and of reproducing in living cells only" (Luria, General Virology, 1st ed., Wiley, New York, 1953), which have more recently been further defined as "entities whose genomes are elements of nucleic acid that replicate inside living cells using the cellular synthetic machinery and causing the synthesis of specialized elements that can transfer the viral genome to other cells" (Luria, et al., General Virology, 3rd ed., Wiley, New York, 1978).

An important group of vector-borne disease agents are the arthropod-borne viruses (arboviruses), most of which are togaviridae or bunyaviridae. In most cases, the arboviruses are maintained in nature by a vector-host cycle that does not include humans. Five families of blood-sucking animals (Culicidae or mosquitoes, Ceratopogonidae or midges, Psychodidae or sand flies, Ixodidae or hard-shell ticks, and Argasidae or soft-shell ticks) are common vectors for the viruses, and various vertebrates, generally wild mammals and birds, serve as host and reservoirs. The virus is maintained only if balanced populations of hosts and vectors exist, and if they are in contact with each other. The persistence of a virus in nature is governed by the arthropod vector rather than the host, since, typically the arthropod is not damaged by the virus.

It has been noted as one of the most interesting properties of the arboviruses, that they multiply both in a vertebrate host at temperatures up to 39° C. or in insects and insect cell cultures at lower temperatures (Hurlbut and Thomas, "The Experimental Host Range of the Arthropod-borne Animal Viruses in Arthropods", Virology, Vol. 12, Pp. 391–407, 1960; and Pfefferkorn and Shapiro, "Reproduction of Togaviruses in Comprehensive Virology", Fraenkel-Conrab and Wagner, ed. Plenum Press, New York, 1974, Pp. 17-230).

Rickettsiae are intracellular parasites that are small gram-negative bacteria which multiply by growth and fission, possess a bacterial-type cell wall which includes a rigid mucopeptide layer, and have an autonomous energy producing system. They are constrained by synthetic and enzymatic deficiencies to intracellular parasitism. The pathogenic rickettsia are primarily parasites of arthropods, and are occasionally also pathogenic for vertebrates. Rickettsial diseases of man vectored by lice, ticks, mites, etc., include epidemic typhus, Rocky Mountain spotted fever, South American spotted fever, fièvre boutonneuse, Q fever, tsutsugamushi disease (scrub typhus), trench fever, and rickettsialpox, and before transmission to man, may be reservoired by rats, wild rodents, field and house mice, cattle, sheep, goats, or man itself, depending upon the particular causal organism.

Patents which appear to relate to this invention are as follows.

U.S. Pat. No. 3,709,782 discloses a heteroploid feline embryonic cell line, the growth of viruses thereon, and vaccines containing such viruses. The disclosed medium is Eagle's Basal Medium with other ingredients, but without Liebovitz's L-15. Moreover, there is no disclosure of non-vertebrate cell lines.

U.S. Pat. No. 4,021,302 is very similar to U.S. Pat. No. 3,709,782, except that the cell line is substantially diploid.

U.S. Pat. No. 4,040,905 discloses a cell line of diploid cells from vertebrates, suitable for virus vaccine production.

U.S. Pat. No. 2,658,021 discloses a production method for vertebrate animal tissue cell lines.

U.S. Pat. No. 3,647,633 discloses an apparatus for the continuous production of microorganisms and plant and animal cell lines.

U.S. Pat. No. 4,017,631 discloses a process for producing continuous tumoral cell lines in vitro.

SUMMARY OF THE INVENTION

This invention provides six new cell lines which were established in continuous culture from embryonic tissues of ticks (Acari: Ixodidae). Four cell lines were from *Dermacentor variabilis* (cell lines RML-15, RML-18, RML-19, and RML-20) and two cell lines were from *Dermacentor parumapertus* (cell lines RML-16 and RML-17). All of the cell lines were substantially fibroblastic.

DESCRIPTION OF THE PREFERRED EMBODIMENTS

Isolation and Tissue Culture

The methods used in this invention for the preparation of the primary cultures have been described in detail in Yunker and Meibos "Culture of Embryonic Tick Cells (Acari: Ixodidae)", supra. Briefly, embryonic cells were extracted from egg masses of 2-4 surface-sterilized females 8-12 days after oviposition. The cells were dispersed in growth medium, lightly centrifuged in two changes of medium, resuspended in 10 ml of medium and divided between two 30 ml plastic flasks. The flasks had been preconditioned by incubation with growth medium at 37° C./24 hr in a $CO_2$ incubator. Primary cultures were incubated at 27° C. in ambient air and medium was changed weekly. Culture medium is critical and consisted of about equal parts of Eagle's minimal essential medium in Hank's base and Liebovitz's L-15 medium, plus about 20% fetal bovine serum inactivated at 56° C. for 1 hr, about 10% tryptose phosphate broth solution, and about 0.1% bovine plasma albumin (fraction V), all adjusted to a pH of about 6.8. The ratio of Eagle's M.E.M. to Liebovitz's L-15 is critical in the establishment of the cell lines, and to maintain the cell lines at optimum, and must be about 1:1. Ratios of 0.5-2:1 of Eagle's M.E.M. to Liebovitz's L-15 are sufficient to maintain the cell lines temporarily, but not to establish cell lines. Antibiotics may optionally be added to the medium, a typical amount being 100 $\mu$/ml penicillin G, 100 $\mu$g/ml streptomycin sulfate; and 40 $\mu$g/ml neomycin sulfate.

The *D. variabilis* cell lines of this invention adapted to an incubation temperature of from about 25° C. up to about 39° C., preferably about 37° C. The *D. parumapertus* cell lines of this invention, adapted to an incubation temperature of from about 25° C. up to about 30° C., preferably about 27° C.

As has now become conventional with cell cultures, the cell lines were identified with alphanumerical designations. The research for this invention having been conducted at the Rocky Mountain Laboratory of the National Institute of Allergy and Infectious Diseases, all cell lines begin with the letters RML-, followed by a number identifying the particular line. Each of the six cell lines of this invention has been deposited with the Americal Type Culture Collection (ATCC), 12301 Parklawn Drive, Rockville, Md. 20852, U.S.A., where the cell lines will be maintained and made available to the public upon request.

The cell lines of this invention may be individually identified by the following table.

TABLE I

| Cell Line | ATCC No. | Source | First Subculture (days) | 37° C. incubation (adaptation passage) | Chromosome complement (male/female) | Activity-Subculture frequency (days/temp °C.) |
|---|---|---|---|---|---|---|
| RML-15 | CRL8052 | Dermacentor variabilis | 86 | 13 | diploid (43/38) | 5.5/37[(2)] |
| RML-16 | CRL8053 | Dermacentor parumapertus | 48 | none[(1)] | aneuploid (5/44) | 7/27 |
| RML-17 | CRL8054 | D. parumapertus | 38 | none[(1)] | aneuploid (3/67) | 21/27 |
| RML-18 | CRL8055 | D. variabilis | 36 | 13 | diploid (62/20) | 10.5/37 |
| RML-19 | CRL8056 | D. variabilis | 38 | 9 | diploid (44/42) | 7/37 |
| RML-20 | CRL8057 | D. variabilis | 79 | 7 | diploid | 10.5/37 |

TABLE I-continued

| Cell Line | ATCC No. | Source | First Subculture (days) | 37° C. incubation (adaptation passage) | Chromosome complement (male/female) | Activity-Subculture frequency (days/temp °C.) |
|---|---|---|---|---|---|---|
| | | | | | (47/14) | |

(1) cannot withstand 37° C., maintained at 27° C. incubation temperature
(2) population doubling time is 70.1 hr at 37° C. and 181.9 hr at 27° C.

Commenting on these cell lines generally, and with specific references to the data in Table I, cells of all four *D. variabilis* lines are morphologically similar but readily distinguishable from those of the two lines, of *D. parumapertus*. Cells of the former species are predominately fibroblastic, with fusiform or stellate outlines and compact cytoplasms. Monolayers formed by these cells are relatively confluent and in order cultures epithelioid patches and scattered small clumps of cells are seen. The two lines of *D. parumapertus* cells are also predominately fibroblastic, but in each the cytoplasm is diffuse, wispy and membranous; patches of epithelial-like cells and numerous spherical forms are also seen. Here, monolayers are incompletely confluent, and thickened foci or cells are large and numerous.

Chromosome complements of all four *D. variabilis* cell lines are mostly diploid [2n=21 (♂) or 22 (♀)]. However, some aneuploids, particularly at lower passage levels, and polyploids at higher passage levels, are evident. In two lines (RML-15 and RML-19), the respective modal frequencies of 80% and 71% are about equally divided between male and female complement; but in the other two (RML-18 and RML-20), the male complement (62%, 47%) predominates over that of the female (20%, 14%). The two *D. parumapertus* cell lines (RML-16 and RML-17), are largely aneuploid, with the female complement more frequent (44%, 67%) than that of the male (5%, 3%). Chromosome morphology for all six lines is characteristic of the genus; the autosomes are significantly shorter than the sex chromosomes and all are apparently acrocentric.

Population doubling time for the RML-15 line is 70.1 hr at 37° C. and 181.9 hr at 27° C. When flasks are incubated at 37° C., the average time between subcultures is 5.5 days. The other three *D. variabilis* lines grow somewhat more slowly at 37° C., averaging 7 days (RML-19) or 10.5 days (RML-18, RML-20) between passages. One line of *D. parumapertus* cells (RML-16) is subcultured at weekly intervals, whereas the other (RML-17) is less active and is subcultured every 21 days. All of the lines described above have been subcultured over 24 times, the RML-15 line having exceeded 72 passages.

Viable cells of all Dermacentor lines, which had been frozen in the presence of 7–10% dimethylsulfoxide, are readily recoverable from frozen storage.

All lines were found to be free of mycoplasmas and other microorganisms when tested at various passage levels by direct culture of antibiotic-free cells and fluorescent staining. Samples from each line were cultured in three mycoplasma broth media (20% horse serum broth, SP-4 broth and a semi-solid mycoplasma medium) and plated on 20% horse serum agar. Samples were also placed in an indicator cell system (standard Vero cells which are a monkey kidney cell line) and cells were removed at intervals and stained with Hoechst DNA stain and a fluorescein-conjugated antiserum to *Mycoplasma hyorhinis*.

The cell lines at various passage levels were tested for the presence of specific adventitious agents, with negative results in all instances.

Utilization of the Cell Strains

The cell lines of this invention may be utilized for replicating viruses, rickettsias, chlamydias, spiroplasms and protozoans. These replicated pathogens can probably be utilized for the production of vaccines, antibodies, antitoxins, and the like. Additional possible uses of replicated pathogens would be to produce antigens for allergic sensitivity testing and for producing biological control agents for ticks, such as arthropod directed pathogens, e.g. Nosema, or microsporidia (which are pathogenic to ticks).

The cell lines of this invention are particularly useful for the replication of pathogens which infect livestock and are arthropod vectored. This is because mammalian cell lines may not produce a high enough titer when infected with arthropod-borne pathogens, possibly because the pathogens require arthropod hosts at some point in their life cycle. Thus, a more potent pathogen strain may be obtained using the cell lines of this invention, which will afford a better vaccine, etc.

For example, *Rickettsia (Cowdria) ruminantium* is the causal agent of heartwater disease in African cattle and is spread by cattle ticks. It causes severe economic loss to the cattle industry in Africa, as well as contributing to infectious disease and malnutrition among peoples of underdeveloped nations by virtue of the limitations it imposes on the raising of cattle. It is believed that laboratory research and development of heartwater vaccine are hampered by the fact that this pathogen is capable of growth only in cattle, cattle ticks, and in primary cultures of tick cells. An inexpensive, replicable laboratory system for the propagation of the organism and production of vaccine is needed, and is afforded by the cell lines of this invention. Cattle are expensive and there are problems involved in rearing adequate numbers of ticks and the preparation of numerous primary cultures of tick cells. In addition, any of the latter systems may themselves contain latent or adventitious agents.

The cell lines of this invention, in addition to the above provide (1) a culture for the production of pathogens of invertebrates, which products may be used in the biological control of vectors of disease, (2) a constant and replicable source of antigens of tick origin, which may be used in the immunization or desensitization of animals against ticks or tick bites, (3) a poikilothermic cell line for the isolation and identification of temperature sensitive variants of pathogenic viruses, which variants may not be detectable in conventional laboratory animals or in homeothermic cell culture systems, (4) a culture in which temperature sensitive variants of arboviruses may be isolated by replicating the arboviruses in any of the cell lines of this invention at an incubation temperature set from about 22° C. to about 36° C. and (5) a culture for the replication of viruses selected from the group consisting of Togaviridae, Reoviridae, Rhabdoviradae, Bunyaviridae, and taxonomically unclassified arboviruses.

Virus Replication Utilizing Cell Lines of This Invention

Two of the *D. variabilis* lines, RML-15 and RML-19, were tested as substrates for arbovirus growth. Medium and cells sampled at intervals from virus-inoculated cultures were tested by plaque assay in Vero or *Xenopus laevis* (XTC-2) cells supplied by the London School of Hygiene and Tropical Medicine, or by intracerebral inoculation of newborn mice. The cells were subjected to a wide variety of arboviruses, which replicated without perceptible cytopathic effect. The results are seen in the following table.

TABLE II

Arbovirus susceptibility of two *Dermacentor variabilis* cell lines

| VIRUS & STRAIN | Cell Line | Incubation T°C. | Virus titer in culture sample[1] | |
|---|---|---|---|---|
| | | | Day 0 | Day 7 |
| Chikungunya (23161) | RML-19 | 27 | 3.1 | 6.7 |
| O'nyong-nyong (MP30) | RML-15 | 27 | 3.3 | 6.0 |
| St. Louis enceph. (798-55) | RML-15 | 27 | 1.9 | 2.8 |
| Yellow fever (17D) | RML-19 | 37 | 2.9 | 5.8 |
| Langat (TP21) | RML-15 | 37 | 3.3 | 5.3 |
| Powassan (794) | RML-15 | 37 | 4.2 | 6.6 |
| Modoc (M544) | RML-15 | 37 | 4.7 | 1.6 |
| Kemerovo (R10) | RML-15 | 37 | 0.9 | 4.0 |
| Colorado tick fever (SS18) | RML-19 | 37 | 3.5 | 5.7 |
| Sawgrass (PR96406) | RML-19 | 37 | 4.5 | 6.3 |
| *D. occidentalis* (Cascade virus) (109213D) | RML-15 | 27 | 2.2 | 5.5 |

[1]Plaque forming units per ml in Vero cells.
Exceptions: St. Louis encephalitis virus titrated in XTC-2 cells;
Langat virus titrated by intracerebral inoculation of suckling mice and titers expressed as LD$_{50}$/ml.

Commenting on Table II, both mosquitoborne and tickborne viruses of the family Togaviridae (Chikungunya, O'nyong-nyong, St. Louis encephalitis, yellow fever, Langat, Powassan) replicated to higher levels, whereas a non-vectorborne Flavivirus, Modoc, did not. The tickborne viruses, Kemerovo and Colorado tick fever (Reoviridae), and Sawgrass (Rhabdoviridae) also grew in these cells. Cascase virus (109231D) from *D. occidentalis* ticks collected in Oregon, which is serologically unrelated to any arbovirus thus far tested and probably new, grew in RML-15 cells at 27° C. The agent had been recovered repeatedly in a poikilothermic cell line (XTC-2) but could not be isolated in Vero cells or intracerebrally inoculated newborn mice. When frozen tick triturates that had originally yielded the virus were thawed and retested in RML-15 cells, isolations were readily made, as revealed by specific immunofluorescence reactions and plaque assay in XTC-2 cells.

Rickettsia Replication Utilizing Cell Lines of This Invention

One each of the *D. variabilis* line, RML-15, and the *D. parumapertus* line, RML-16, were tested as substrates for rickettsial growth. Medium and cells sampled at intervals from rickettsia-inoculated cultures were tested by plaque assay in Vero or *Xenopus laevis* (XTC-2) cells supplied by the London School of Hygiene and Tropical Medicine or are expressed as the Infectious Dose (ID$_{50}$) determined by serological conversion of intraperitoneally inoculated adult mice, as measured by an indirect immunofluorescence test. The cell lines were subjected to a variety of rickettsias.

TABLE III

Susceptibility of two lines of Dermacentor cells to infection with various rickettsias

| RICKETTSIAS (species & strain) | Cell Line | Incubation T°C. | Rickettsial titer per ml of culture sample[1] | | post inoculation day sampled |
|---|---|---|---|---|---|
| | | | inoculated | recovered | |
| *R. rickettsii* (R) | RML-15 | 34 | 1.0 | 5.7 | 7 |
| *R. akari* (Kaplan) | RML-15 | 34 | 1.0 | 5.3 | 13 |
| *R. typhi* (Wilmington) | RML-15 | 34 | 3.6 | 8.8 | 14 |
| argasid tick isolate (113704-14) | RML-15 | 27 | 2.5 | 4.5 | 6 |
| argasid tick isolate (113704-14) | RML-16 | 27 | 2.5 | 4.7 | 6 |

[1]Plaque forming units per ml in Vero cells (*R. rickettsii, R. akari*) or XTC-2 cells (argasid tick isolates).
Exception: *R. typhi* expressed as ID$_{50}$ determined by serological conversion of intraperitoneally inoculated adult mice, as measured by indirect immunofluorescence test.

The results shown in Table III demonstrate the ability of the tick cells of this invention to be useful in the replication of rickettsias of various serological groups.

All rickettsias tested thus far replicated to higher levels in the tick cell lines of this invention. This replication was, in some instances, as great as about $1 \times 10^5$ or $1 \times 10^6$ in the relatively short period of time in which the tests were conducted. This indicates a potential usefulness in vaccine production.

We claim:

1. A continuous cell line of embryonic cells of Acari: Ixodidae of the species *Dermacentor variabilis* designated RML-15 and having ATCC No. CRL 8052.

2. A continuous cell line of embryonic cells of Acari: Ixodidae of the species *Dermacentor variabilis* designated RML-18 and having ATCC No. CRL 8055.

3. A continuous cell line of embryonic cells of Acari: Ixodidae of the species *Dermacentor variabilis* designated RML-19 and having ATCC No. CRL 8056.

4. A continuous cell line of embryonic cells of Acari: Ixodidae of the species *Dermacentor variabilis* designated RML-20 and having ATCC No. CRL 8057.

5. A continuous cell line of embryonic cells of Acari: Ixodidae of the species *Dermacentor parumapertus* designated RML-16 and having ATCC No. CRL 8053.

6. A continuous cell line of embryonic cells of Acari: Ixodidae of the species *Dermacentor parumapertus* designated RML-17 and having ATCC No. CRL 8054.

7. The cell line of claims 1, 2, 3 or 4 adapted to an incubation temperature of from about 25° C. up to about 39° C.

8. The cell line of claim 7 adapted to an incubation temperature of about 37° C.

9. The cell line of claim 5 or 6 adapted to an incubation temperature of from about 25° C. to about 30° C.

10. The cell line of claim 9 adapted to an incubation temperature of about 27° C.

11. A composition consisting essentially of the cell line of any one of claims 1 to 6 maintained in a sterile medium consisting essentially of: modified Liebovitz-15 medium with glutamine and Eagle's minimal essential medium with Hank's salts and glutamine in a ratio of about 0.5–2:1; to which have been added: about 20% fetal bovine serum inactivated at 56° C. for 1 hr; about 10% tryptose phosphate broth; and about 0.1% bovine plasma albumin-fraction V; all adjusted to a pH of about 6.8.

12. The composition of claim 11 wherein after establishment, the cell line is maintained in a culture medium in which the ratio of modified Liebovitz-15 medium with glutamine to Eagle's minimal essential medium with Hank's salts and glutamine is about 1:1.

13. A method of replicating a microorganism selected from one of the group consisting of viruses, rickettsias, and spiroplasms, comprising infecting the cell line of any one of claims 1 to 6 with said microorganism and incubating the infected culture.

14. The method of claim 13 wherein the microorganism is a virus selected from the group consisting of Chikungunya (23161), O'nyong-nyong (MP30), St. Louis encephalitis (798-55), Yellow fever (17D), Langat (TP21), Powassan (794), Modoc (M544), Kemerovo (R10), Colorado Tick Fever (SS18), Sawgrass (PR96406), and Cascade Virus (109231D).

15. The method of claim 13 wherein the cell line infected consists essentially of cells of the species *Dermacentor variabilis.*

16. The method of claim 13 wherein the microorganism is a rickettsia selected from the group consisting of *R. Rickettsii* (R), *R. akari* (Kaplan), *R. typhi* (Wilmington), and argasid tick isolate (113704-14).

17. The method of claim 13 wherein the microooganism is a virus selected from the group consisting of Togaviridae, Reoviridae, Rhabdoviridae, Bunyaviridae, and taxonomically unclassified Arboviruses.

18. A method of isolating temperature sensitive variants of arboviruses comprising replicating the arboviruses in the cell line of any one of claims 1 to 6 at an incubation temperature set at from about 22° C. to about 36° C. and isolating the replicated variants.

* * * * *